United States Patent
Muraoka et al.

(10) Patent No.: US 7,534,811 B2
(45) Date of Patent: May 19, 2009

(54) CYCLIC ONIUM COMPOUNDS AND GLUCOSIDASE INHIBITORS

(75) Inventors: Osamu Muraoka, Higashiosaka (JP); Masayuki Yoshikawa, Minoo (JP); Genzoh Tanabe, Osaka (JP); Hisashi Matsuda, Kyoto (JP)

(73) Assignees: Kinki University, Osaka (JP); Diabetym Co., Ltd., Osaka (JP)

( * ) Notice: Subject to any disclaimer, the term of this patent is extended or adjusted under 35 U.S.C. 154(b) by 0 days.

(21) Appl. No.: 10/559,768

(22) PCT Filed: May 31, 2004

(86) PCT No.: PCT/JP2004/007487

§ 371 (c)(1), (2), (4) Date: Dec. 22, 2006

(87) PCT Pub. No.: WO2004/111028

PCT Pub. Date: Dec. 23, 2004

(65) Prior Publication Data

US 2007/0135486 A1   Jun. 14, 2007

(30) Foreign Application Priority Data

Jun. 12, 2003   (JP) ............... 2003-167786

(51) Int. Cl.
*A61K 31/381* (2006.01)
*A61K 31/382* (2006.01)
*C07D 333/32* (2006.01)
*C07D 335/02* (2006.01)

(52) U.S. Cl. .......... 514/432; 514/445; 549/28; 549/66

(58) Field of Classification Search ............ 514/348, 514/445, 432; 549/66, 28; 546/290
See application file for complete search history.

(56) References Cited

U.S. PATENT DOCUMENTS

| | | | |
|---|---|---|---|
| 5,097,023 A | 3/1992 | Ducep et al. | |
| 5,157,116 A | 10/1992 | Ducep et al. | |
| 6,455,573 B1 | 9/2002 | Pinto et al. | |

FOREIGN PATENT DOCUMENTS

| | | |
|---|---|---|
| JP | 54-106477 | 8/1979 |
| JP | 2-025498 | 1/1990 |
| JP | 3-127797 | 5/1991 |
| JP | 2001-103928 | 4/2001 |
| JP | 2002-51735 | 2/2002 |
| JP | 2002-104979 | 4/2002 |
| JP | 2002-179673 | 6/2002 |
| WO | WO 0149674 | 7/2001 |

OTHER PUBLICATIONS

Dec. 1, 1997 "Salacinol, Potent Antidiabetic Principle with Unique Thiosugar Sulfonium Sulfate Structure from the Ayurvedic Traditional Medicine Salacia reticulata in Sri Lanka and India." Masatuki Yoshikawa et al. Tetrahedron Letters vol. 38 No. 48 8367-8370.

*Primary Examiner*—Taofiq A Solola
(74) *Attorney, Agent, or Firm*—Jordan and Hamburg LLP

(57) ABSTRACT

Cyclic onium compounds reresented by the following structural formula (I), glucosidase inhibitors using such compounds, and antidiabetic drugs or food containing such glucosidase inhibitor.

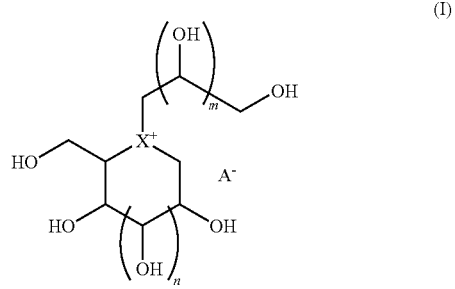

wherein $A^-$ is an aniom; m is an interger between 1 and 6, n is 0 or 1, $X^+$ is $S^+$ or $N^+Q$ (where Q is H or an alkyl of 1 to 4 carbon atoms).

14 Claims, No Drawings

CYCLIC ONIUM COMPOUNDS AND GLUCOSIDASE INHIBITORS

BACKGROUND OF THE INVENTION

1. Field of the Invention

The present invention relates to novel cyclic onium compounds; more specifically, it relates to cyclic sulfonium compounds and cyclic ammonium compounds useful as a glucosidase inhibitor for inhibiting the glycolytic activity of glucosidase, and a glucosidase inhibitor using these compounds.

2. Description of Related Art

Use of a glucosidase inhibitor that inhibits glycolytic activity of the glycolytic enzyme glucosidase can suppress absorption and digestion of sugar in the intestines, etc. Thus there are hopes for the usefulness of glucosidase inhibitors as a drug for treatment or prevention of diabetes. Known examples of compounds used as such a glucosidase inhibitor include cyclic sulfonium compounds such as a thiacyclopentane derivative and thiacyclohexane derivative where the sulfur atoms have a valence of 3.

For example, claim 8 of JP 2002-179673 (patent document 1) discloses as a compound having glucosidase-inhibiting activity a cyclic sulfonium compound represented by the following structural formula (III):

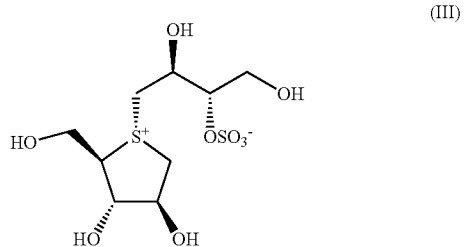

Meanwhile, Tetrahedron Letters, Vol. 38, No. 48. pp. 8367-8370 (1997) (non-patent document 1) discloses that salacinol, which is an essential pharmacological substance contained in the medicinal plant *salacia reticulata* used in traditional medicine in India, is a powerful glucosidase inhibitor, and the structural formula of salacinol is further disclosed. The cyclic sulfonium compound of formula (III) has a structure similar to that of the salacinol and demonstrates similar glucosidase-inhibiting activity.

Further, JP 2002-51735 (patent document 2), for example, discloses an antidiabetic food containing salacinol.

It is an object of the present invention to provide a cyclic sulfonium compound and cyclic ammonium compound having glucosidase-inhibiting activity equivalent or superior to those of known glucosidase inhibitors such as salacinol.

The inventors of the present invention discovered, following careful examination of a variety of cyclic sulfonium compounds and cyclic ammonium compounds, that novel cyclic sulfonium compounds that are thiacyclopentane derivatives or thiacyclohexane derivatives with a specific structure and cyclic ammonium compounds with a specific structure have superior glucosidase-inhibiting activity, and thus made the present invention.

[Patent document 1] JP 2002-179673 A (claim 8)
[Patent document 2] JP 2002-51735 A (paragraph no. 8)
[Non-patent document] Tetrahedron Letters, Vol. 38, No. 48. pp. 8367-8370 (1997)

BRIEF SUMMARY OF THE INVENTION

The present invention provides a cyclic onium compound represented by the following structural formula (I):

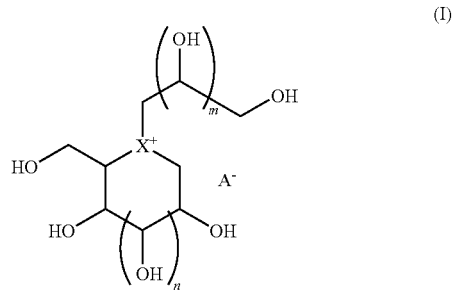

wherein $A^-$ is an anion, m is an integer between 1 to 6, n is 0 or 1, $X^+$ is $S^+$ or $N^+Q$ (where Q is H or an alkyl having 1 to 4 carbon atoms).

The present invention further provides a cyclic onium compound as a specific and more preferable form of the cyclic onium compound of structural formula (I) above. As a more particularly preferable form, a cyclic sulfonium compound represented by the following structural formula (II) is provided:

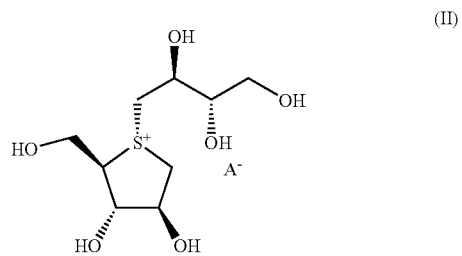

The present invention also provides a glucosidase inhibitor containing the above cyclic onium compound and an antidiabetic drug or food containing such glucosidase inhibitor.

DETAILED DESCRIPTION

The present invention will be explained in detail.

The cyclic onium compound represented by the structural formula (I) above contains sulfonium compounds wherein $X^+$ is $S^+$ and cyclic ammonium compounds wherein $X^+$ is $N^+Q$ (where Q is H or an alkyl having 1 to 4 of carbons atoms).

$X^+$ is preferably $S^+$ or $N^+H$, and of these $S^+$ is more preferable. More specifically, a cyclic onium compound represented by the formula (I) is preferably a cyclic sulfonium compound.

Examples of such a cyclic sulfonium compound include a thiacyclopentane derivative wherein n in the formula (I) is 0 and a thiacyclohexane wherein n in the formula (I) is 1.

In structural formula (I), m is an integer between 1 and 6 and is preferably 2 or 5.

A preferable example is a thiacyclopentane derivative wherein m is 2, n is 0, and $X^+$ is $S^+$, more specifically, a cyclic sulfonium compound represented by the following structural formula (IV).

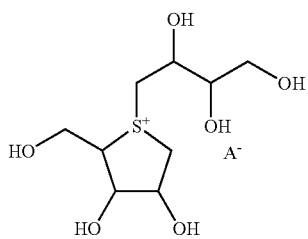

wherein A⁻ is an anion.

Of the cyclic sulfonium compounds represented by the structural formula (IV), a cyclic sulfonium compound represented by the structural formula (II) above has excellent glucosidase-inhibiting activity and is particularly preferable.

Examples of anions represented by A⁻ in the formulae (I), (II), and (IV) include halogen ions such as $F^-$, $Cl^-$ $Br^-$, and $I^-$; anions originating from Lewis acid such as $BF_4^-$; $R^1$—$SO_3^-$; $R^1$—$CO_2^-$ (wherein $R^1$ is an alkyl having 1 to 4 carbon atoms or an alkyl halide); $R^2$—$OSO_3^-$ (wherein $R^2$ is an alkyl having 1 to 4 carbon atoms); phosphate ions; and $ClO_4^-$.

Of those examples illustrated above, an anion is preferably selected from the group consisting of halogen ions, anions originating from Lewis acid, $R^1$—$SO_3^-$, and $R^2$—$OSO_3^-$, and more preferably $R^2$—$OSO_3^-$ or $Cl^-$, and even more preferably $CH_3OSO_3^-$ or $Cl^-$). More specifically, among the cyclic onium compounds of the present invention the most preferable glucosidase inhibitor is a compound represented by the following structural formula (or a compound wherein $CH_3OSO_3^-$ in the above mentioned compound is substituted by $Cl^-$):

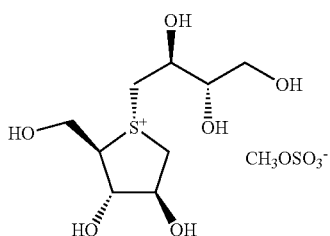

While no particular limitations are made with respect to the production method for the cyclic onium compound of the present invention, the cyclic onium compound of the present invention can be obtained, for example, by solvolysis of salacinol and the like.

Also, the cyclic sulfonium compound of the formula (V) can be obtained by adding salacinol to methanol in which hydrogen chloride is dissolved, and performed solvolysis while maintaining the temperature at roughly 40° C. Production methods for salacinol are disclosed in JP 2002-179673 A (patent document 1), etc.

In addition, a cyclic sulfonium compound represented by the formula (II) wherein A⁻ is $CZ_3SO_3^-$ (where Z is H or a halogen) can be obtained using an isoascorbic acid in accordance with the following synthesis route:

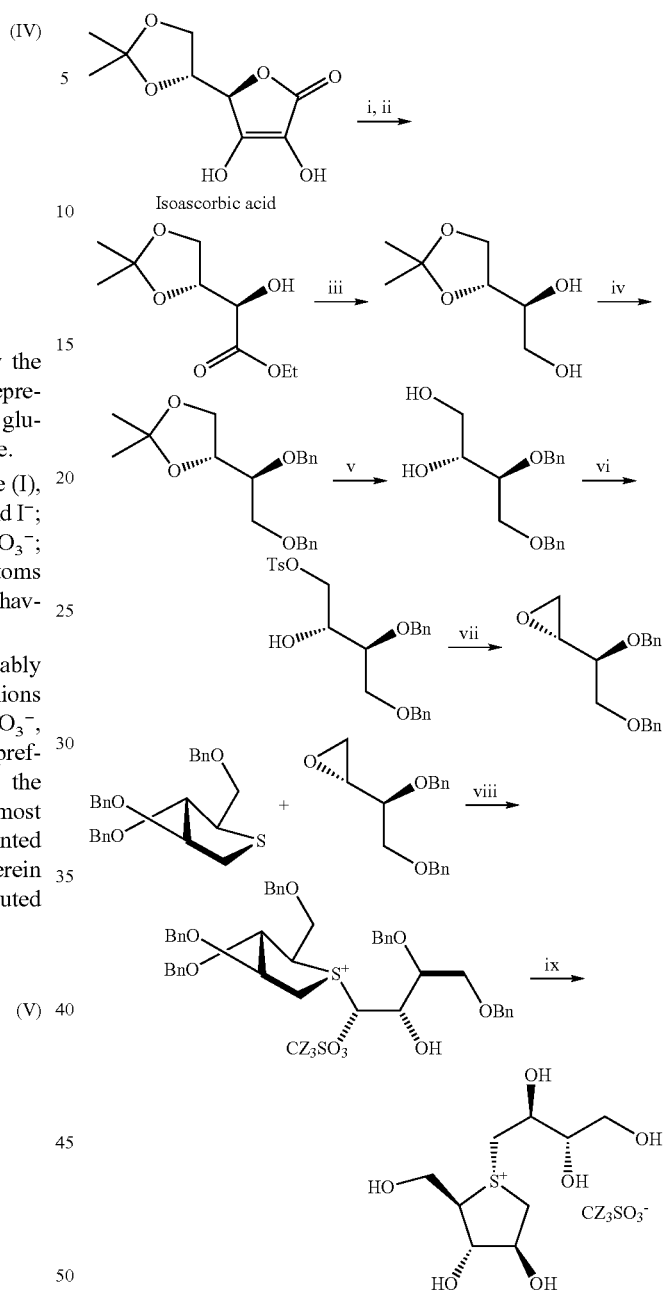

wherein Bn is benzyl, Et is ethyl, Ts is paratoluenesulfonyl, and Z is H or halogen.

The preferable conditions for the respective steps of the synthesis route above are as follows.

i) $K_2CO_3$, 30% aqueous $H_2O_2$ solution, 20° C.
ii) EtI, $CH_3CN$, reflux temperature
iii) $LiAlH_4$, THF, room temperature
iv) BnBr, NaH, DMF, room temperature
v) EtOH, concentrated hydrochloric acid, room temperature
vi) TsCl, pyridine, 0° C.
vii) NaH, THF, room temperature
viii) $CZ_3SO_3H$ (Z has the meaning given above), $CH_2Cl_2$, room temperature
ix) Pd/C, $H_2$ The cyclic sulfonium compounds and cyclic ammonium compounds of the present invention inhibit glycolytic activity of glucosidase such as maltase, saccharase, and isomaltase. More specifically, the presence of a cyclic sulfonium compound and cyclic ammonium compound of the present invention inhibits maltase and saccharase and the like from breaking down maltose and sucrose and the like into glucose. Therefore, the cyclic sulfonium compounds and cyclic ammonium compounds of the present invention can be used as a glucosidase inhibitor.

Further, administration of a cyclic sulfonium compound or cyclic ammonium compound of the present invention inhibits, by the glucosidase-inhibiting activities thereof, the intestinal glycolytic action of glucosidase such as maltase and saccharase. Accordingly, digestion and absorption of sugar by the intestinal tract is suppressed. Therefore, a pharmaceutical composition or a food containing a glucosidase inhibitor containing the cyclic sulfonium compound or cyclic ammonium compound of the present invention can exhibit an excellent effect as an antidiabetic drug or food, a dietary food, and the like.

The present invention will be explained in detail using examples, but the examples are not to be construed as limiting the scope of the invention.

EXAMPLE 1

28 mg (0.08 mmol) of salacinol having the structure of the structural formula (III) was dissolved in 0.6 ml of methanol containing 5% hydrogen chloride. The solution was then allowed to react at 40° C. for 3 hours to obtain 27 mg (yield at 93%) of the cyclic sulfonium compound represented by the structural formula (V). The resulting compound shall be referred to as Compound 1.

Measurement of Compound 1 was performed with respect to optical rotation, infrared absorption spectrum, $^1$H-NMR, $^{13}$C-NMR, and mass analysis (FAB (Fast Atom Bombardment)-MS and HR-FAB-MS). The results of the measurement are as follows:

$[\alpha]_D^{20}$+3.6 (c=1.08, CH$_3$OH) IR (neat): 3321, 1420, 1207 cm$^{-1}$ $^1$H-NMR (CD$_3$OD) (chemical shift): 3.60 (1H, m), 3.62 (1H, dd, J=12.9, 5.2 Hz, H-4'a), 3.67 (3H, s, CH$_3$OSO$_3^-$), 3.68 (1H, dd, J=12.9, 4.6 Hz, H-4'b), 3.72 (1H, dd, J=13.2, 8.9 Hz, H-1'a), 3.84 (1H, dd, J=13.2, 3.2 Hz, H-1'b), 3.85 (1H, dd, J=12.6, 2.0 Hz, H-1a), 3.87 (1H, dd, J=12.6, 2.0 Hz, H-1b), 3.92 (1H, dd, J=10.3, 8.9 Hz, H-5a), 4.01 (1H, br dd, J=8.9, 5.2 Hz, H-4), 4.05 (1H, dd, J=10.3 5.2 Hz, H-5b), 4.08 (1H, ddd, J=8.9, 5.7, 3.2 Hz, H-2'), 4.37 (1H, br d-like, J=1.5 Hz, H-3), 4.62 (1H, br d-like, J=2.0 Hz, H-2) $^{13}$C-NMR (CD$_3$OD) (chemical shift): 51.8 (C-1'), 52.0 (C-1), 55.2 (CH$_3$OSO$_3^-$), 61.0 (C-5), 64.0 (C-4'), 69.6 (C-2'), 73.7 (C-4), 75.3 (C-3'), 79.4 (C-2), 79.5 (C-3) FAB-MS m/z: 255 [M-CH$_3$OSO$_3$]$^+$ (pos.), 111[CH$_3$OSO$_3$]$^-$(neg.) HR-FAB-MS m/z: 255.0912 (C$_9$H$_{19}$O$_6$S requires 255.0903)

EXAMPLE 2

16 mg (0.044 mmol) of Compound 1 obtained in Example 1 and 290 mg of a cation exchange resin IRA-400 (Cl$^-$ type) were added to a mixed solvent of methanol (0.3 ml) and water (0.5 ml). The solution was stirred at room temperature for 12 hours to obtain 12.2 mg (yield at 96%) of the cyclic sulfonium compound represented by the structural formula (II) wherein A is Cl$^-$.

Measurement of the resulting compound was performed with respect to optical rotation, infra-red absorption spectrum, $^1$H-NMR, $^{13}$C-NMR, and mass analysis (FAB (Fast Atom Bombardment)-MS and HR-FAB-MS). The results of the measurement are as follows:

$[\alpha]_D^{20}$+5.9 (C=0.8, CH$_3$OH) IR (neat): 3325, 1420, 1076 cm$^{-1}$ $^1$H-NMR (CD$_3$OD) (chemical shift): 3.60 (1H, m), 3.62 (1H, dd, J=12.9, 5.2 Hz, H-4'a), 3.68 (1H, dd, J=12.9, 5.7 Hz, H-4'b), 3.73 (1H, dd, J=13.2, 8.9 Hz, H-1'a), 3.84 (1H, dd, J=13.2, 3.2 Hz, H-1'b), 3.85 (1H, dd, J=12.6, 2.3 Hz, H-1a), 3.87 (1H, dd, J=12.6, 2.3 Hz, H-1b), 3.92 (1H, dd, J=10.3, 8.6 Hz, H-5a), 4.01 (1H, br dd, J=8.6, 5.5 Hz, H-4), 4.05 (1H, dd, J=10.3, 5.5 Hz, H-5b), 4.08 (1H, ddd, J=8.9, 6.3, 3.2 Hz, H-2'), 4.37 (1H, br d-like, J=1.5 Hz, H-3), 4.62 (1H, br d-like, J=2.3 Hz, H-2) $^{13}$C-NMR (CD$_3$OD) (chemical shift): 51.8 (C-1'), 52.1 (C-1), 61.0 (C-5), 64.0 (C-4'), 69.6 (C-2'), 73.7 (C-4), 75.3 (C-3'), 79.4 (C-2), 79.5 (C-3) FAB-MS m/z: 255 [M-Cl]$^+$ (pos.) HR-FAB-MS m/z: 255.0915 (C$_9$H$_{19}$O$_6$S requires 255.0903)

COMPARATIVE SYNTHESIS EXAMPLE 1

5.0 g (11.6 mmol) of the tri-O-benzylthiosugar represented by the following structural formula (F) and 1.1 g (46.5 mmol) of metallic sodium were added to a mixture of approximately 60 ml liquid ammonium and 30 ml tetrahydrofuran. The resulting solution was then stirred at a reaction temperature of between −70 and −60° C. for an hour to obtain 1.3 g (yield at 74%) of the compound represented by the structural formula (G):

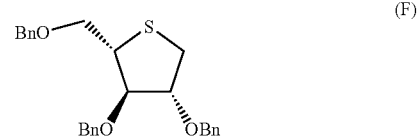

wherein Bn is a benzyl.

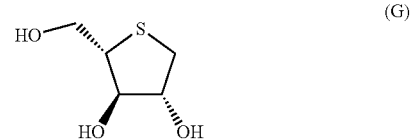

A mixture of 500 mg (3.3 mmol) of the resulting compound represented by the structural formula (G), 708 mg (3.6 mmol) of silver tetrafluoborate and 0.3 ml of methyl iodine were added to a mixed solvent of approximately 60 ml of liquid ammonium and 30 ml of tetrahydrofuran. The solution was stirred at room temperature for 22 hours and allowed to react. As a result, 779 mg of the compound represented by the following structural formula (VI) was obtained (91% yield). The resulting compound shall be referred to as Compound 2. Compound 2 was a diastereomeric mixture with different stereochemical structures (α:β=approximately 3.2:1.0).

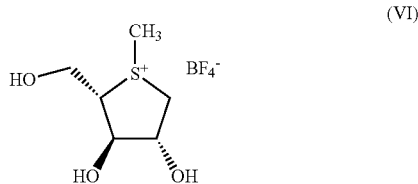

Measurement of Compound 2 was performed with respect to optical rotation, infrared absorption spectrum, $^1$H-NMR, $^{13}$C-NMR, and mass analysis (FAB (Fast Atom Bombardment)-MS and HR-FAB-MS). The results of the measurement are as follows:

$[\alpha]_D^{23}$ −6.64 (c=1.25, H$_2$O) $^1$H-NMR (500 MHz, CD$_3$OD) major: (chemical shift): 3.09 (3H, s), 3.70 (1H, dd, J=3.4, 12.6 Hz), 3.84 (1H, dd, J=2.3, 12.6 Hz), 3.83-3.87 (1H, m), 3.90 (1H, dd, J=9.8, 11.5 Hz), 4.03 (1H, dd, J=4.9, 11.5 Hz), 4.36 (1H, br d-like), 4.64 (1H, br dt-like, J=2.3, 3.4 Hz). minor: (chemical shift) 3.13 (3H, s), 3.45 (1H, br d, J=13.8 Hz), 3.45 (1H, br d, J=4.0, 13.8 Hz), 4.09 (1H, t, J=10.6, 10.6 Hz), 4.12 (1H, ddd, J=2.3, 3.8, 10.6 Hz), 4.21 (1H, dd, J=3.8, 10.6 Hz), 4.39 (1H, br d-like), 4.57 (1H, dt, J=2.0, 2.2, 4.0 Hz) $^{13}$C-NMR (125 MHz, CD$_3$OD) major: (chemical shift) 28.7 (q), 51.5(t), 60.9(t), 74.3(d), 79.5(d), 80.0(d). minor: (chemical shift) 21.6 (q), 48.8(t), 58.8(t), 67.9(d), 80.1(d), 80.2 (d) HR-FAB-MS m/z: 165.0581(C$_6$H$_{13}$O$_3$S requires 165.0585)

EXAMPLE 3

Measurement of Concentration for 50% Inhibition

Rat intestinal brush border membrane vesicles were prepared, and a suspension in a 0.1M maleic acid salt buffer solution (pH6.0) was used as small intestinal α-glucosidase (maltase and saccharase).

0.05 ml of sample compound solutions of differing concentration were added, respectively, to 0.1 ml of a substrate solution of sucrose (74 mM) and maltose (74 mM), and the solution was preheated at 37° C. for 2 to 3 minutes. 0.05 ml of an enzymatic solution was added thereto and the solution was allowed to incubate for 30 minutes. After incubation, 0.8 ml of water was added thereto and the solution was heated in a boiling water bath for 2 minutes to deactivate the enzyme. Blank was prepared as follows. After the enzymatic solution was added to each sample, water was immediately added, and the resulting mixture was heated in a boiling water bath for 2 minutes to deactivate the enzyme. The amount of d-glucose formed therein was measured using a glucose oxidase method. The substrate and test samples were dissolved in a 0.1M maleic acid buffer solution (pH6.0). The concentrations for 50% inhibition (IC$_{50}$) were calculated based on the values obtained.

TABLE 1

| Test Compounds | | IC$_{50}$ (μg/ml) | |
| --- | --- | --- | --- |
| Type | Amount (mg) | Sucrose | Maltose |
| Compound 1 | 4.5 | 1.35 | 5.71 |
| Compound 2 | 5.2 | 56.0 | 79.3 |

As is clear from the results shown in Table 1, Compound 1, which is within the scope of the present invention, exhibits excellent glucosidase-inhibiting activity. On the other hand, Compound 2, which is outside the scope of the present invention, does exhibit glucosidase inhibiting activity, but such activity is lower than that of Compound 1.

The cyclic onium compounds of the present invention have excellent glucosidase-inhibiting activity. Therefore, the cyclic sulfonium compound and cyclic ammonium compound of the present invention can be used as superior glucosidase inhibitors. In addition, by including therein the cyclic sulfonium compound and cyclic ammonium compound of the invention, superior antidiabetic drugs or foods, or dietary foods can be obtained.

The invention claimed is:

1. Cyclic onium compounds represented by the following structural formula (I)

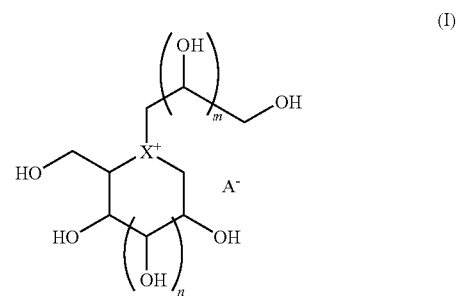

wherein A$^-$ is an anion; m is an integer between 1 and 6, n is 0, and X$^+$ is S$^+$.

2. Cyclic onium compounds according to claim 1 Wherein m is 2 or 5.

3. Cyclic onium compounds represented by the following structural formula (II):

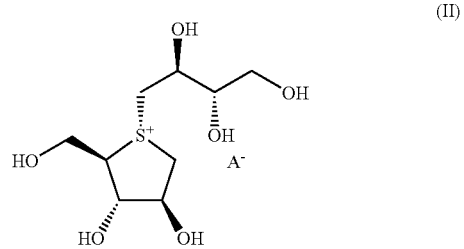

wherein A$^-$ is an anion.

4. Cyclic onium compounds according to any of claims 1, 2, or 3 wherein A$^-$ is selected from the group consisting of halogen ions, Lewis acid ions, R$^1$—SO$_3$$^-$ (wherein R$^1$ is an alkyl of 1 to 4 carbon atoms or an alkyl halide), and R$^2$—OSO$_3$$^-$ (wherein R$^2$ is an alkyl of 1 to 4 carbon atoms).

5. Cyclic onium compounds according to claim 1 wherein A$^-$ is selected from the group consisting of halogen ions, anions originating from Lewis acid, R$^1$—SO$_3$$^-$ (wherein R$^1$ is an alkyl of 1 to 4 carbon atoms or an alkyl halide), or R$^2$—OSO$_3$$^-$ (wherein R$^2$ is an alkyl of 1 to 4 carbon atoms).

6. Cyclic onium compounds according to claim 4 wherein A$^-$ is CH$_3$—OSO$_3$$^-$ or Cl−.

7. Cyclic onium compounds according to claim 5 wherein A$^-$ is CH$_3$—OSO$_3$$^-$ or Cl−.

8. Antidiabetic drugs or food containing a glucosidase inhibitor according to any of claims 1, 2 or 3.

9. Antidiabetic drugs or food containing the glucosidase inhibitor according to claim 1.

10. Antidiabetic drugs or food containing the glucosidase inhibitor according to claim 4.

11. Antidiabetic drugs or food containing the glucosidase inhibitor according to claim 5.

12. Antidiabetic drugs or food containing the glucosidase inhibitor according to claim 4.

13. Antidiabetic drugs or food containing the glucosidase inhibitor according to claim 7.

14. The cyclic onium compound of claim 1 wherein m is an integer between 2 and 5.

* * * * *